United States Patent [19]

Sprague

[11] 4,086,244
[45] Apr. 25, 1978

[54] AMIDINES

[75] Inventor: Peter W. Sprague, Titusville, N.J.

[73] Assignee: E. R. Squibb & Sons, Inc., Princeton, N.J.

[21] Appl. No.: 748,861

[22] Filed: Dec. 10, 1976

[51] Int. Cl.² .......................................... C07D 319/08
[52] U.S. Cl. ............................... 260/340.3; 424/278; 260/465 F; 260/564 RF
[58] Field of Search ..................................... 260/340.3

[56] References Cited
PUBLICATIONS
Chem. Abstracts 80:27227t.

Primary Examiner—Ethel G. Love
Attorney, Agent, or Firm—Lawrence S. Levinson; Merle J. Smith; Donald J. Barrack

[57] ABSTRACT

Compounds having the formula

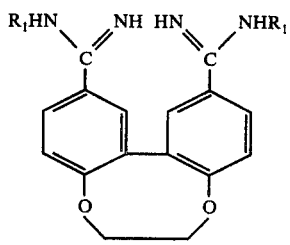

and the pharmaceutically acceptable salts thereof, wherein $R_1$ is aryl, have useful antiinflammatory activity.

6 Claims, No Drawings

AMIDINES

BRIEF DESCRIPTION OF THE INVENTION

Compounds having the formula

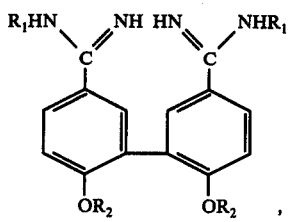

and the pharmaceutically acceptable salts thereof, have useful antiinflammatory activity. In formula I, and throughout the specification the symbols are as defined below.

$R_1$ is phenyl or phenyl substituted with one or two methoxy, halogen, or trifluoromethyl groups.

$R_2$ is hydrogen or alkyl, or both $R_2$ groups together form an ethylene group.

The term "alkyl", as used throughout the specification, refers to alkyl groups having 1 to 12 carbon atoms.

The term "halogen", as used throughout the specification, refers to fluorine, chlorine, bromine and iodine.

DETAILED DESCRIPTION OF THE INVENTION

The compounds of this invention are prepared using as starting materials compounds having the formulas

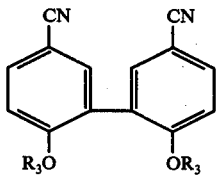

and

In formula II, and throughout the specification, both $R_3$ groups are hydrogen or alkyl.

Reaction of a 6,6'-dialkoxy[1,1'-biphenyl]-3,3'-dicarbonitrile of formula II ($R_3$ is alkyl) and an aniline derivative of formula III, in the presence of a reducing agent (sodium hydride is preferred) yields the corresponding compound of formula I wherein $R_2$ is alkyl. The reaction can be run in an organic solvent, preferably a polar organic solvent such as dimethylsulfoxide or dimethylformamide. Conditions under which the reaction is run are not critical, and it can conveniently be carried out at room temperature.

Those compounds of formula I wherein $R_2$ is hydrogen can be prepared by cleaving the alkyl groups of a corresponding diether of formula I (wherein $R_2$ is alkyl) with an acid. Pyridine hydrochloride has been found to be as effective acid reagent.

Those compounds of formula I wherein the $R_2$ groups together form an ethylene group, i.e., compounds having the formula

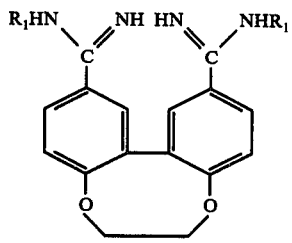

can be prepared by first reacting 6,6'-dihydroxy[1,1'-biphenyl]-3,3'-dicarbonitrile (formula II, $R_3$ is hydrogen) with a compound having the formula $$X-CH_2-CH_2-Y, \qquad (V)$$

wherein X and Y are independently selected from halogen (chlorine and bromine are preferred), alkylsulfonate and arylsulfonate, to yield a compound having the formula

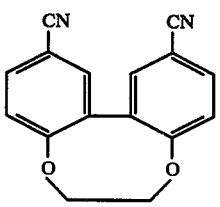

The reaction can be run at an elevated temperature in an organic solvent, preferably a polar organic solvent such as dimethylsulfoxide or dimethylformamide, in the presence of a base, e.g., sodium carbonate.

Reaction of a compound of formula VI and an aniline derivative of formula III in the presence of a reducing agent (sodium hydride is preferred) yields the corresponding compound of formula IV. The reaction can be run in an organic solvent, preferably a polar organic solvent such as dimethylsulfoxide or dimethylformamide. Conditions under which the reaction is run are not critical, and it can conveniently be carried out at room temperature.

The starting materials of formula II are known, or readily prepared in accordance with art recognized procedures; see, for example, Leupold et al., *Ann. Chem.*, 746, 134–148 (1971).

The pharmaceutically acceptable salts of the compounds of formula I can be prepared from the corresponding free base using procedures well known in the art. Acid-addition salts are specifically contemplated, e.g., the hydrohalides (especially the hydrochloride and hydrobromide), sulfate, nitrate, phosphate, tartrate, maleate, fumarate, citrate, succinate, methanesulfonate, benzenesulfonate, toluenesulfonate and the like.

The compounds of formula I, and the pharmaceutically acceptable salts thereof, are useful for the treatment of inflammation in mammalian species, such as rats, dogs, cats, monkeys, etc. Joint tenderness and stiffness (in conditions such as rheumatoid arthritis) can be relieved by the above-described compounds.

The compounds of this invention can be formulated for use as antiinflammatory agents according to accepted pharmaceutical practice in oral dosage forms such as tablets, capsules, elixirs or powders, or in an injectable form in a sterile aqueous vehicle prepared according to conventional pharmaceutical practice.

The compounds of this invention can be administered in amounts of 100 milligrams per kilogram of animal body weight per day to 2 grams per kilogram of animal body weight per day, preferably 100 milligrams per kilogram of animal body weight per day to 1 gram per kilogram of animal body weight per day.

The following examples are specific embodiments of this invention.

EXAMPLE 1

6,6'-Dimethoxy-N,N''-diphenyl[1,1'-biphenyl]-3,3'-dicarboximidamide, hydrochloride (1:2)

A mixture of 4.0 g of 6,6'-dimethoxy[1,1'-biphenyl]-3,3'-dicarbonitrile, 1,5 g of sodium hydride (50% suspension in oil), 2.8 g of aniline and 15 ml of dimethylsulfoxide is prepared and stirred at room temperature for about 16 hours under nitrogen. The mixture is then poured into water and the precipitate which forms is separated with filtration. The residue is recrystallized twice from 10% hydrochloric acid to yield 7.0 g of the title compound which is dried over phosphorous pentoxide under vacuum for 12 hours, to yield the title compound, melting point 220°–230° C dec.

Anal. Calc'd. for $C_{28}H_{28}N_4O_2Cl_2 4H_2O$: C, 56.47; H, 6.09; N, 9.41; Cl, 11.91. Found: C, 56.27; H, 6.07; N, 9.30; Cl, 11.86.

EXAMPLE 2

6,6'-Dihydroxy-N,N''-diphenyl[1,1'-biphenyl]-3,3'-dicarboximidamide, hydrochloride (1:2)

A mixture of 2.5 g of 6,6'-dimethoxy-N,N''-diphenyl[1,1'-biphenyl]-3,3'-dicarboximidamide, monohydrochloride (see Example 1) and 25 g of dry pyridine hydrochloride is heated at 180° C for 75 minutes. The mixture is then cooled, diluted with 10 ml of water and acidified with 10 ml of concentrated hydrochloric acid. The mixture is further diluted with 100 ml of 10% hydrochloric acid and allowed to stand at 0° C for about 16 hours. The crystalline material so obtained is recrystallized from dilute HCl (10% hydrochloric acid and water until solution occurs at 100° C) to yield 900 mg of the title compound, melting point 306°–307° C.

Anal. Calc'd. for $C_{26}H_{22}N_4O_2 . 2$ HCl: C, 63.03; H, 4.88; N, 11.31; Cl, 14.31. Found: C, 63.09; H, 4.80; N, 11.26; Cl, 14.10.

EXAMPLE 3

6,6'-Dimethoxy-N,N''-[3-(trifluoromethyl)phenyl][1,1'-biphenyl]-3,3'-dicarboximidamide, hydrochloride (1:2)

A mixture of 4.00 g of 6,6'-dimethoxy[1,1'-biphenyl]-3,3'-dicarbonitrile, 1.5 g of sodium hydride (50% suspension in mineral oil), and 5.0 g of m-trifluoromethylaniline is prepared in 15 ml of dimethylsulfoxide and stirred for about 16 hours under nitrogen at room temperature. The resulting reaction mixture is diluted with water and the precipitate which forms is filtered with suction. The residue is purified by suspension in water followed by acidification and filtration. The filtrate is neutralized with 10% sodium hydroxide solution and the precipitate collected by filtration. This residue is then recrystallized twice from 10% hydrochloric acid yielding 2.0 g of the title compound, melting point 220°–230° C, dec.

Anal. Calc'd. for $C_{30}H_{32}N_4O_4F_6Cl_2$: C, 51.66; H, 4.64; N, 8.03; Cl, 10.16. Found: C, 51.46; H, 4.52; N, 7.73; Cl, 10.34.

EXAMPLE 4

N,N''-Bis(3,5-dimethoxyphenyl)-6,6'-dimethoxy[1,1'-biphenyl]-3,3'-dicarboximidamide, hydrochloride (1:2)

A mixture of sodium hydride (57% in mineral oil, 1.52 g), 3,5-dimethoxyaniline (4.6 g), and 6,6'-dimethoxy[1,1'-biphenyl]-3,3'-dicarbonitrile (4.0 g) in anhydrous dimethylsulfoxide (15 ml) is stirred under nitrogen at room temperature for 18 hours. The dark oil obtained is poured into water and the resultant precipitate collected by filtration. The solid is slurried in water and the pH adjusted to pH 5 with 10% hydrochloric acid. This treatment dissolves most of the precipitate. The solution is then filtered to remove traces of starting material. The solution is made basic with 10% sodium hydroxide and the resultant precipitate is collected by filtration and washed with water. This material is recrystallized twice from 10% hydrochloric acid and once from 5% hydrochloric acid to yield 2.8 g of the title compound, melting point 228°–230° C, dec.

Anal. Calc'd. for $C_{32}H_{34}N_4O_6 . 2$ HCl: C, 59.72; H, 5.64; N, 8.71; Cl, 11.02. Found: C, 59.97; H, 5.64; N, 8.69; Cl, 10.94.

EXAMPLE 5

N,N''-Bis(4-Fluorophenyl)-6,6'-dimethoxy[1,1'-biphenyl]-3,3'-dicarboximidamide, hydrochloride (1:2)

A mixture of 6,6'-dimethoxy[1,1'-biphenyl]-3,3'-dicarbonitrile (5.0 g) and sodium hydride (1.92 g) is prepared in dimethylsulfoxide (20 ml). To this is added, with stirring under nitrogen, a solution of p-fluoroaniline (3.8 g) dissolved in 10 ml of dimethylsulfoxide. The addition is carried out at such a rate as to control the foaming that occurs in this reaction. After addition is complete, the mixture is stirred at room temperature for 24 hours and poured into water. The precipitate which forms is separated by filtration and the residue washed on the filter with water. The material is recrystallized twice from 10% hydrochloric acid to yield 8.3 g of the title compound, melting point 229° C, dec.

Anal. Calc'd. for $C_{28}H_{24}F_2N_4O_2.2$ HCl.2 $H_2O$: C, 56.47; H, 5.09; N, 9.41, F, 6.38; Cl, 11.91. Found: C, 56.66; H, 5.14; N, 9.46; F, 6.53; Cl, 11.96.

EXAMPLE 6

6,7-Dihydro-N,N''-diphenyldibenzo[e,g][1,4]dioxocin-2,11-dicarboximidamide

A.

6,7-Dihydrodibenzo[e,g][1,4]dioxocin-2,11-dicarbonitrile

A mixture of 6,6'-dihydroxy[1,1'-biphenyl]-3,3'-dicarbonitrile (11.8 g), sodium carbonate (10.6 g), and 1,2-dibromoethane (8.4 g) in 250 ml of anhydrous dimethylformamide is heated at 150° C for 18 hours under nitrogen. The reaction mixture is poured into water and extracted with three 200 ml portions of dichloromethane. The dichloromethane extracts are combined and washed with 10% sodium hydroxide, water, and brine. The solution is filtered through 100 ml of silica gel and concentrated. The resultant solid is recrystallized from benzene to yield 3.5 g of the title compound, melting point 195°–196° C.

Anal. Calc'd. for $C_{16}H_{10}N_2O_2$: C, 73.27; H, 3.84; N, 10.68. Found: C, 73.43; H, 3.67; N, 10.74.

B.
6,7-Dihydro-N,N''-diphenyldibenzo[e,g][1,4]dioxocin-2,11-dicarboximidamide

A slurry of 6,7-dihydrodibenzo[e,g][1,4]dioxocin-2,11-dicarbonitrile (2.62 g), aniline (1.86 g) and sodium hydride (50% in oil, 960 mg) in anhydrous dimethylsulfoxide (30 ml) is stirred at room temperature under nitrogen for 24 hours. The reaction mixture is poured into water and the resultant precipitate collected by filtration. The crude product (4 g) is washed on the filter several times with water. A sample of this crude product (100 mg) is recrystallized from benzene/cyclohexane to yield 75 mg of the title compound, melting point 201°–205° C, dec.

Anal. Calc'd. for $C_{28}H_{24}N_4O_2$: C, 74.98; H, 5.39; N, 12.49. Found: C, 74.86; H, 5.55; N, 12.20.

EXAMPLE 7

6,7-Dihydro-N,N''-diphenyldibenzo[e,g][1,4]-dioxocin-2,11-dicarboximidamide, hydrochloride (1:2)

A crude sample of 6,7-dihydrodibenzo[e,g][1,4]-dioxocin-2,11-dicarbonitrile (2.5 g, see Example 6A) is recrystallized three times from 10% hydrochloric acid to yield 1.5 g of the title compound, melting point 237°–242° C, dec.

Anal. Calc'd. for $C_{28}H_{24}N_4O_2 \cdot 2$ HCl $\cdot \frac{3}{4}$ H$_2$O: C, 62.86; H, 5.18; N, 10.48; Cl, 13.25. Found: C, 62.78; H, 5.23; N, 10.27; Cl, 13.19.

EXAMPLE 8

6,7-Dihydro-N,N''-bis(4-methoxyphenyl)dibenzo[e,g][1,4]-dioxocin-2,11-dicarboximidamide A mixture of 2.62 g of 6,7-dihydrodibenzo[e,g][1,4]-dioxocin-2,11-dicarbonitrile (see Example 6A), 0.96 g of sodium hydride (50% mineral oil) and 2.46 g of p-anisidine is prepared in dimethylsulfoxide (15 ml) and stirred under nitrogen for 24 hours at room temperature. The mixture is then poured into water and the precipitate which forms is separated by filtration. This compound is recrystallized from methanol to yield 1.5 g of the title compound, melting point 343°–345° C, plus a second crop of 500 mg.

Anal. Calc'd. for $C_{30}H_{28}N_4O_4$ (first crop): C, 68.44; H, 5.74; N, 10.64. Found: C, 68.39; H, 5.95; N, 10.38.

EXAMPLE 9

6,7-Dihydro-N,N''-bis[3-(trifluoromethyl)phenyl]-dibenzo[e,g][1,4]-dioxocin-2,11-dicarboximidamide, hydrochloride (1:2)

A mixture of 2.5 g of 6,7-dihydrodibenzo[e,g][1,4]-dioxocin-2,11-dicarbonitrile (see Example 6A) and sodium hydride (960 mg) is prepared under nitrogen at room temperature in dimethylsulfoxide (10 ml). To this is added m-aminobenzotrifluoride (3.1 g) in dimethylsulfoxide (4 ml) at such a rate as to control the tendency of this reaction to foam. The combined reaction mixture is stirred for 24 hours at room temperature and then poured into water. The precipitate which forms is separated by filtration and washed with water yielding 4.5 g of solid. This is crystallized by dissolving first in ether followed by gradual addition of cyclohexane with much scratching with a glass rod. In this way 3.5 g of free base, melting point 206°–212° is obtained. A hydrochloride is prepared from this by dissolving in dilute hydrochloric acid (just enough HCl to reach a pH of 5) followed by addition of concentrated hydrochloric acid. The crystalline hydrochloride so obtained is dried for 24 hours at room temperature over phosphorous pentoxide, yielding 2.4 g of the title compound, melting point 236°–240° C.

Anal. Calc'd. for $C_{30}H_{24}N_4F_6Cl_2O_2 + 1.5$ mole H$_2$O:C, 52.64; H, 3.98; N, 8.18; Cl, 10.36. Found: C, 52.80; H, 3.80; N, 8.20; Cl, 10.37.

EXAMPLE 10

N,N''-Bis(4-fluorophenyl)-6,7-dihydrodibenzo[e,g][1,4]-dioxocin-2,11-dicarboximidamide, hydrochloride (1:2)

A mixture of 2,5 g of 6,7-dihydrodibenzo[e,g][1,4]-dioxocin-2,11-dicarbonitrile (see Example 6A) and sodium hydride (960 mg) is prepared in dimethylsulfoxide (10 ml) under nitrogen. To this is added p-fluoroaniline (2.14 g) dissolved in 4 ml of dimethylsulfoxide at a rate slow enough to control the foaming of the reaction mixture. After addition is complete the reaction mixture is stirred under nitrogen for 24 hours and then poured into water. The precipitate which forms is separated by filtration and washed on the filter with water yielding, after drying, 4.0 g of free base. This is recrystallized from acetonitrile to yield 2.5 g of pure material, melting point 259°–262°. A hydrochloride is prepared by recrystallization of the free base from dilute hydrochloric acid, yielding 2.3 g of the title compound, melting point 273°–725° C.

Anal. Calc'd. for $C_{28}H_{22}F_2N_4O_2$ 2 HCl H$_2$O:C, 58.44; H, 4.55; N, 9.74; F, 6.60; Cl, 12.32. Found: C, 58.72; H, 4.55; N, 9.81; F, 6.61; Cl, 12.58.

EXAMPLE 11

6,6'-Bis(pentyloxy)-N,N''-bis[3-(trifluoromethyl)-phenyl][1,1'-biphenyl]-3,3'-dicarboximidamide, hydrochloride (1:2)

A. 6,6'-Dipentyloxy[1,1'-biphenyl]-3,3'-dicarbonitrile

Sodium hydride (50% in oil, 1.92 g) is washed with pentane and slurried in 50 ml of anhydrous dimethylformamide. The slurry is treated with 6,6'-dihydroxy[1,1'-biphenyl]-3,3'-dicarbonitrile (4.72 g), heated at 130° C for 2 hours, and treated with 1-bromopentane (6.04 g). The reaction mixture is heated at 130° C for 3 days and the mixture is poured into water and extracted with dichloromethane. After washing with water and brine, the dichloromethane extract is dried over sodium sulfate and concentrated. The residue is chromatographed on silica gel (800 ml) eluting with hexane/dichloromethane (1:1) to yield 5.4 g of the title compound, melting point 70°–71° C.

B.
6,6'-Bis(pentyloxy)-N,N''-bis[3-(trifluoromethyl)-phenyl]-[1,1'-biphenyl]-3,3'-dicarboximidamide, hydrochloride (1:2)

A slurry of sodium hydride (50% in oil, 1.76 g), m-aminobenzotrifluoride (5.91 g) and 6,6'-dipentyloxy[1,1'-biphenyl]-3,3'-dicarbonitrile (6.9 g; additional material is added to the batch of part (A) in 50 ml of anhydrous dimethylsulfoxide is stirred at room temperature for 3 days. The reaction mixture is poured into water and the resultant precipitate collected by filtration. The dried material is chromatographed on 1 liter of silica gel eluting with (1) dichloromethane and (2) 1% methanol/dichloromethane to yield 5'-cyano-2',6-bis(pentyloxy)-N-[3-(trifluoromethyl)phenyl][1,1'- biphenyl]-3-carboximidamide (melting point 74°–75° C after 2 recrystallizations from cyclohexane). The column is next eluted with 2% methanol/dichloromethane to yield 1.3 g of the desired product. Two recrystallizations of this material from 1% hydrochloric acid/methanol yields 900 mg of the title compound, melting point 207°–210° C.

Anal. Calc'd. for $C_{38}H_{40}N_4O_2F_6 \cdot 2HCl \cdot H_2O$:

C, 57.80; H, 5.62; N, 7.09; Cl, 8.98. Found: C, 57.80; H, 5.47; N, 6.87; Cl, 9.05.

EXAMPLE 12

6,6'-Bis(dodecyloxy)-N,N''-bis[3-(trifluoromethyl)-phenyl]-[1,1'-biphenyl]-3,3'-dicarboximidamide, hydrochloride (1:2)

A. 6,6'-Didodecyloxy[1,1'-biphenyl]-3,3'-dicarbonitrile

Sodium hydride (50% in oil, 1.92 g) is washed with pentane and slurried in 50 ml of anhydrous dimethylformamide. A solution of 6,6'-dihydroxy[1,1'-biphenyl]-3,3'-dicarbonitrile (4.72 g) in 5 ml of anhydrous dimethylformamide is added to the slurry and the mixture is heated at 150° C for 2 hours, after which 1-bromododecane (9.96 g) is added. The reaction is heated at 150° C for 3 days and the reaction mixture is poured into water and extracted with dichloromethane. After washing with water and brine, the dichloromethane extract is dried over sodium sulfate and concentrated in vacuo. The residue is chromatographed on silica gel (800 ml) eluting with hexane/dichloromethane (1:1) to yield 7.4 g of the title compound, melting point 94°–95° C. B. 6,6'-Bis(dodecyloxy)-N,N''-bis[3-(trifluoromethyl)-phenyl]-[1,1'-biphenyl]-3,3'-dicarboximidamide, hydrochloride (1:2)

A slurry of sodium hydride (50% in oil, 1.42 g), m-aminobenzotrifluoride (4.74 g) and 6,6'-dihydroxy[1,1'-biphenyl]-3,3'-dicarbonitrile (7.6 g) in 50 ml of dimethylsulfoxide is stirred at room temperature for 3 days. The reaction mixture is poured into water and the resultant solid collected by filtration. The dried solid is chromatographed on 1 liter of silica gel eluting with (1) dichloromethane, (2) 0.5% methanol/dichloromethane and (3) 2% methanol/dichloromethane to yield 5.9 g of desired product, which is treated with 5 ml of concentrated hydrochloric acid and recrystallized from water/methanol to yield 4 g of the title compound, melting point 168°–170° C.

Anal. Calc'd. for $C_{52}H_{68}F_6N_4O_2 \cdot 2HCl \cdot H_2O$: C, 63.34; H, 7.36; N, 5.68; Cl, 7.19. Found: C, 63.05; H, 7.11; N, 5.71; Cl, 7.37.

What is claimed is:

1. A compound having the formula

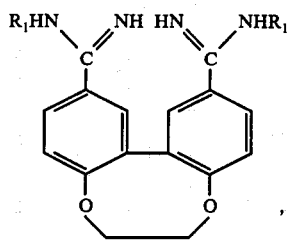

or a pharmaceutically acceptable salt thereof, wherein $R_1$ is phenyl or phenyl substituted with one or two methoxy, halogen, or trifluoromethyl groups.

2. The compound in accordance with claim 1 having the name 6,7-dihydro-N,N''-diphenyldibenzo[e,g][1,4]-dioxocin-2,11-dicarboximidamide.

3. The compound in accordance with claim 1 having the name 6,7-dihydro-N,N''-diphenyldibenzo[e,g][1,4]-dioxocin-2,11-dicarboximidamide, hydrochloride (1:2).

4. The compound in accordance with claim 1 having the name 6,7-dihydro-N,N''-bis(4-methoxyphenyl)-dibenzo[e,g]-[1,4]dioxocin-2,11-dicarboximidamide.

5. The compound in accordance with claim 1 having the name 6,7-dihydro-N,N''-bis[3-(trifluoromethyl)-phenyl]-dibenzo[e,g][1,4]dioxocin-2,11-dicarboximidamide, hydrochloride (1:2).

6. The compound in accordance with claim 1 having the name N,N''-bis(4-fluorophenyl)-6,7-dihydrodibenzo[e,g][1,4]-dioxocin-2,11-dicarboximidamide, hydrochloride (1:2).

* * * * *